United States Patent
Banavali et al.

(10) Patent No.: US 7,582,784 B2
(45) Date of Patent: Sep. 1, 2009

(54) METHOD FOR TRANSESTERIFICATION OF TRIGLYCERIDES

(75) Inventors: Rajiv Manohar Banavali, Rydal, PA (US); Abraham Benderly, Elkins Park, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 11/827,490

(22) Filed: Jul. 12, 2007

(65) Prior Publication Data

US 2008/0015375 A1 Jan. 17, 2008

Related U.S. Application Data

(60) Provisional application No. 60/830,972, filed on Jul. 14, 2006.

(51) Int. Cl.
*C11B 1/00* (2006.01)

(52) U.S. Cl. ..................................... 554/169

(58) Field of Classification Search ........................ None
See application file for complete search history.

(56) References Cited

U.S. PATENT DOCUMENTS 5,606,103 A    2/1997   Trapasso et al.
5,908,946 A    6/1999   Stern et al.
6,878,837 B2   4/2005   Bournay et al.
2005/0107624 A1  5/2005  Lin et al.
2005/0113588 A1  5/2005  Hillion et al.
2005/0261509 A1  11/2005 Delfort et al.

FOREIGN PATENT DOCUMENTS

EP    1 785 478           5/2007
KR    2002/028118         4/2002
WO    WO 2005063954 A1 *  7/2005

OTHER PUBLICATIONS

Abreu et al., Journal of Molecular Catalysis, vol. 227, pp. 263-267, 2005.*
Angiolini, et al., "Cross-linked resins functionalized with triorganotin carboxylates: synthesis , . . . ", Applied Organometallic Chemistry, vol. 19, pp. 841-847, (2005).
Lee, et al., "Role of sulfonic acids in the Sn-catalyzed transesterification of dimethyl carbonate with phenol", Catalysis Today, 87, pp. 139,144 (2003).
Abreu, et al., "New multi-phase catalytic systems based on tin compounds active for vegetable oil . . . ", J.Molecular Catalysis A:, Chemical, 227, pp. 263-267 (2005).

* cited by examiner

*Primary Examiner*—Deborah D Carr
(74) *Attorney, Agent, or Firm*—Kenneth Crimaldi

(57) ABSTRACT

A method for transesterification of triglycerides, especially those containing free fatty acids, with methanol. The method uses a catalyst derived from an acidic ion exchange resin. The catalyst is contacted with a reaction mixture containing a triglyceride and methanol under conditions suitable for transesterification.

16 Claims, No Drawings

METHOD FOR TRANSESTERIFICATION OF TRIGLYCERIDES

This application claims the benefit of priority under 35 U.S.C. §119(e) of U.S. Provisional Patent Application No. 60/830,972 filed on Jul. 14, 2006.

BACKGROUND

This invention relates generally to a method for transesterification of triglycerides with methanol to produce fatty acid methyl esters.

High fuel prices and environmental concerns are driving development of alternative fuels, especially those derived from renewable resources. One such fuel, commonly known as "biodiesel" fuel, contains methyl esters of fatty acids, and is burned in diesel engines. Biodiesel fuel is produced from transesterification of triglycerides, such as vegetable oils, with methanol. For example, Abreu, F. R. et al.; in Journal of Molecular Catalysis A: Chemical (2005), 227(1-2), 263-267; demonstrated that the tin compound $Sn(3-hydroxy-2-methyl-4-pyrone)_2(H_2O)_2$ exhibited high catalytic activity for the methanolysis of vegetable oil. However, when this compound was immobilized on an ion exchange resin to facilitate re-use of the catalyst, it lost all activity.

The problem addressed by this invention is to find an improved method for transesterification of triglycerides with methanol, especially those containing significant levels of free fatty acids (1-99%).

STATEMENT OF INVENTION

The present invention is directed to a method for transesterification of triglycerides with methanol; said method comprising steps of: (a) providing a catalyst comprising a metal oxide or metal complex immobilized on an ion exchange resin having acid functionality; and (b) contacting said catalyst with a reaction mixture comprising a triglyceride and methanol under conditions suitable for transesterification.

DETAILED DESCRIPTION

All percentages are weight percentages, and all temperatures are in ° C., unless otherwise indicated. Weight percentages of ion exchange resin are based on dry resin. An "alkyl" group is a saturated hydrocarbyl group having from one to twenty carbon atoms in a linear, branched or cyclic arrangement. Substitution on alkyl groups of one or more halo, hydroxy, alkoxy or nitro groups is permitted; alkoxy substituents may in turn be substituted by one or more halo substituents where possible. Preferably, alkyl groups have no halo substituents, and in one preferred embodiment, alkyl groups are unsubstituted and acyclic. "Triglycerides" used in this invention are fats or oils comprising glycerine triesters of fatty acids. Preferably, triglycerides are in the form of vegetable oils, but animal fats can also be used as a starting material. Triglycerides also may contain free fatty acids. Fatty acids are acyclic aliphatic carboxylic acids containing from 8 to 20 carbon atoms; typically, they contain from 12 to 18 carbon atoms. With respect to carbon-carbon bonds, the fatty acids may be saturated, monounsaturated or polyunsaturated (typically 2 or 3 carbon-carbon double bonds). Natural fats may also contain small amounts of other esterified, or free fatty acids, as well as small amounts (1-4%) of phospholipids, e.g., lecithin, and very small amounts (<1%) of other compounds, e.g., tocopherols.

In one embodiment of the invention, the reaction mixture is heated in a temperature range from 45° C. to 120° C. for at least 0.5 hours. Alternatively, the temperature is at least 50° C., alternatively at least 55° C., alternatively at least 60° C. Alternatively, the temperature is no greater than 100° C., alternatively no greater than 85° C., alternatively no greater than 80° C., alternatively no greater than 75° C. Alternatively, the reaction time is at least 1 hour, alternatively at least 2 hours, alternatively at least 3 hours, alternatively at least 6 hours. Alternatively, the reaction time is no greater than 24 hours, alternatively no greater than 18 hours, alternatively no greater than 14 hours. In an embodiment where the temperature is no greater than 75° C., the reaction time is at least 3 hours. The catalyst is removed from the reaction mixture by filtration, centrifugation, or any other standard method for separating solids and liquids. Glycerol obtained from the transesterification reaction may be removed as part of a separate liquid phase, or by any other suitable separation technique, e.g., centrifugation, distillation.

In one embodiment of the invention, the triglyceride contains from 1% to 99% free (unesterified) fatty acids, alternatively up to 50%, alternatively up to 40%, alternatively up to 30%, alternatively up to 20%, alternatively up to 10%. In one embodiment, the triglyceride contains at least 1% free fatty acids, alternatively at least 2%, alternatively at least 3%, alternatively at least 5%. In this embodiment, the catalyst facilitates esterification of the free fatty acids to their methyl esters, as well as transesterification of triglycerides. Esterification of free fatty acids is desirable to increase the yield of methyl esters, and also to avoid problems resulting from contamination of the reaction mixture and/or the product with free fatty acids, including foaming in the reaction mixture. Previous methods have used separate esterification and transesterification steps to produce biodiesel fuels from oils containing significant concentrations of free fatty acids. In one embodiment of the invention, the triglyceride contains from 2% to 40% free fatty acids.

In one embodiment of the invention, the metal oxide or metal complex is an amphoteric compound. In one embodiment, the metal is Sn, Zn, Ge(II), Cu(II), Ni(II), Fe(II), Fe(III), Al(III), Pt(IV), V(IV) or V(V). Especially preferred metals are Sn, Zn, Ni, Al and Pt as oxides or complexes with other ligands such as sulfides. In one embodiment of the invention, the metal complex is a dialkyl metal oxide, and the alkyl groups in the dialkyl metal oxide are $C_1$ to $C_{10}$ alkyl groups, alternatively $C_2$ to $C_4$ alkyl groups, alternatively n-butyl groups. A particularly preferred dialkyl metal oxide is dibutyl tin oxide (DBTO). The catalyst is formed by immobilizing the metal oxide and/or dialkyl metal oxide on the ion exchange resin by heating the oxide and the resin together with a solvent. Preferred solvents include, e.g., methanol, tetrahydrofuran, dialkyl ethers, toluene, and other organic solvents not having hydroxy or amino groups. In one embodiment, the oxide and the resin are combined at a temperature from 25° C. to 120° C., alternatively from 40° C. to 80° C.; the temperature is maintained for at least 0.25 hours, alternatively at least 0.5 hours, alternatively at least 1 hour. In one embodiment of the invention, the amount of metal oxide is sufficient to complex from 5% to 50% of the acid functionality of the resin, alternatively from 10% to 20%. In one embodiment of the invention, one mole of metal oxide or dialkyl metal oxide complexes two moles of acid groups. For a typical acidic ion exchange resin having from 0.4 to 8 meq/kg acid functionality, preferably an amount of metal oxide and/or dialkyl metal oxide from 10% to 50% of the meq/kg of total dry resin weight is added, alternatively from 15% to 35%. In one embodiment of the invention, the ion exchange resin is a macroreticular resin having a surface area from 25 m²/g to 200 m²/g and an average pore diameter from 50 Å to 500 Å; alternatively a surface area from 30 m²/g to 80 m²/g and an average pore diameter from 100 Å to 300 Å. In one embodiment of the invention, the ion exchange resin comprises polymerized units of styrene and a crosslinker, e.g., divinylbenzene. Preferably, the level of crosslinker is from 1% to 25%. In one embodiment of the invention, the acid functionality of the ion exchange resin comprises sulfonic acid groups, carboxylic acid groups, phosphoric acid groups or a mixture thereof.

EXAMPLES

Example 1

Transesterification of Corn Oil Containing Stearic Acid

In a three-necked flask equipped with a Soxhlet condenser (containing 75 g activated molecular sieves 3A), thermometer and mechanical stirrer, was added a mixture consisting of corn oil (104.8 g), stearic acid (5.79 g; 5.2% of oil+stearic acid), Amberlyst™ 45 ion exchange resin (6.0 g), DBTO (5.9 g) and methanol (303.0 g). The mixture was allowed to reach reflux temperature (~64° C.) with rigorous stirring (250 rpm). Initially, the mixture developed foam which subsided after refluxing for 1 hour.

The process was carried out at 64° C.-65° C. (reflux temperature) and atmospheric pressure for 3 hours. At this point, ~8 ml sample was removed, which after filtering the solid catalyst, separated into two phases, a methanolic phase on top containing a mixture of methyl esters of fatty acid and a bottom phase of mainly unreacted corn oil. After 11 hours, the mixture was cooled to ambient temperature (the course of the reaction was not followed with GC analysis; therefore, the exact time of the completion of the reaction was not determined). The mixture consisted of a single liquid phase.

The ion exchange catalyst was recovered by filtration from the organic phase. After the filtration step, the methanol was evaporated resulted in 115 g of residual oils. Again, the residue consists of one phase only incorporating in it the glycerol and the tin catalyst. The addition of water (27.4 g) formed a precipitate (presumably the tin catalyst+glycerol). The solid was centrifuged resulting in two phases only, which was added to the organic phase and white paste (12.3 g), presumably a mixture of the tin catalyst together with glycerol. The organic phase was washed again with brine solution (54 g), dried over MgSO₄ anhydrous and after gravity filtration the solvent was evaporated resulting in 89.5 g of biodiesel fuel.

High-resolution GC/MS analysis of the starting corn oil and reaction mixture was conducted to analyze for esters. It indicated the presence of mixture of methyl esters of fatty acids {typical biodiesel mixture (methyl esters of palmitic, stearic, linoleic and linolenic acids, etc)} and the presence of stearic acid. The analysis also revealed the presence of glycerol.

It appears that the transesterification process has proceeded in the presence of the spiked stearic acid as confirmed by the presence of various methyl esters. As expected the esterification of stearic acid has progressed also as the presence of methyl ester of stearic acid is confirmed quantitatively by GC-MS. The analysis indicated that about 80-90% conversion of stearic acid/triglycerides took place in first 3 hrs. and at the end of 11 hrs. the conversion was about 92-100%.

TABLE 1

Biodiesel from Corn oil + Stearic Acid

| Fatty acid | % in corn oil | % adjusted for Stearic acid addition | % Methyl esters after 3 hr | % Methyl esters after 3 hr (repeat) | % Methyl esters after 11 hr |
|---|---|---|---|---|---|
| Myristic | 0-2 | 0-2 | — | | |
| Palmitic | 7-11 | 7-11 | 15.6 | 16.1 | 16.3 |
| Stearic | 3-4 | 8-9 | 7.1 | 7.2 | 8.3 |
| Palmitoleic | 0-2 | 0-2 | — | | |
| Oleic | 43-49 | 40-44 | 31 | 33.1 | 33.5 |
| Linoleic | 34-42 | 34-42 | 40.7 | 33.4 | 36.8 |
| Others | — | — | 3.8 | 7.3 | 3.6 |
| % stearic acid/ester | 3.5% | | Total: 98.2*% (7.1/98.2 × 100%) = 7.2% | Total: 97.1*% (7.2/97.1 × 100%) = 7.4% | Total: 98.5% (8.3/98.5 × 100%) = 8.4% |

The invention claimed is:

1. A method for transesterification of fats or oils comprising glycerine triesters of fatty acids with methanol; said method comprising steps of:
   (a) providing a catalyst comprising a metal oxide selected from the group consisting of oxides of Sn, Zn, Ge(II), Cu(II), Ni(II), Fe(II), Fe(III), Al(III), Pt(IV), V(IV) and V(V) immobilized on an ion exchange resin having sulfonic acid functionality; and
   (b) contacting said catalyst with a reaction mixture comprising said fats or oils and methanol at a temperature from 45° C. to 100° C.

2. The method of claim 1 in which the reaction mixture is heated in a temperature range from 55° C. to 80° C. for at least 0.5 hours.

3. The method of claim 2 in which said metal oxide is a dialkyl tin oxide.

4. The method of claim 3 in which alkyl groups in the dialkyl tin oxide are $C_2$ to $C_4$ alkyl groups.

5. The method of claim 1 in which said fats or oils comprise from 1% to 99% free fatty acids.

6. The method of claim 5 in which the reaction mixture is heated in a temperature range from 55° C. to 80° C. for at least 0.5 hours.

7. The method of claim 6 in which said metal oxide is a dialkyl tin oxide.

8. The method of claim 7 in which alkyl groups in the dialkyl tin oxide are $C_2$ to $C_4$ alkyl groups.

9. The method of claim 8 in which said fats or oils comprise 1% to 20% free fatty acids.

10. The method of claim 9 in which said dialkyl tin oxide is dibutyl tin oxide.

11. The method of claim 4 in which said dialkyl tin oxide is dibutyl tin oxide.

12. The method of claim 10 in which the reaction mixture is heated in a temperature range from 60° C. to 75° C. for at least 3 hours.

13. The method of claim 11 in which the reaction mixture is heated in a temperature range from 60° C. to 75° C. for at least 3 hours.

14. The method of claim 12 in which said fats or oils are vegetable oils.

15. The method of claim 13 in which said fats or oils axe vegetable oils.

16. The method of claim 6 in which said fats or oils comprise 1% to 20% free fatty acids.

* * * * *